(12) United States Patent
Lemme et al.

(10) Patent No.: US 7,270,785 B1
(45) Date of Patent: *Sep. 18, 2007

(54) AUTOMATED MOLECULAR PATHOLOGY APPARATUS HAVING FIXED SLIDE PLATFORMS

(75) Inventors: Charles D. Lemme, Tucson, AZ (US); William Richards, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 572 days.

This patent is subject to a terminal disclaimer.

(21) Appl. No.: 10/283,639

(22) Filed: Oct. 30, 2002

Related U.S. Application Data

(60) Provisional application No. 60/350,273, filed on Nov. 2, 2001.

(51) Int. Cl.
*B32B 5/02* (2006.01)

(52) U.S. Cl. ............... 422/64; 422/62; 422/63; 422/65; 422/99; 422/100; 422/101; 436/46; 436/180

(58) Field of Classification Search .......... 422/99–101, 422/63–65; 436/180, 46
See application file for complete search history.

(56) References Cited

U.S. PATENT DOCUMENTS

| | | | |
|---|---|---|---|
| 3,219,416 A | 11/1965 | Natelson | |
| 3,574,064 A | 4/1971 | Binnings et al. | |
| 3,650,437 A | 3/1972 | Binnings et al. | 222/136 |
| 3,665,148 A | 5/1972 | Yasenchak et al. | 219/125 |
| 3,695,281 A | 10/1972 | Leon | 137/1 |
| 3,853,092 A | 12/1974 | Amos et al. | 118/56 |
| 3,854,703 A | 12/1974 | Gibbs et al. | 259/11 |
| 3,900,289 A | 8/1975 | Liston | 23/230 |
| 3,977,568 A | 8/1976 | Smith | |
| 3,979,576 A | 9/1976 | Janson | 219/489 |
| 4,013,038 A | 3/1977 | Rogers et al. | 118/5 |
| 4,043,292 A | 8/1977 | Rogers et al. | 118/5 |
| 4,058,367 A | 11/1977 | Gilford | 23/253 |
| 4,092,952 A | 6/1978 | Wilkie et al. | 118/58 |
| 4,245,967 A | 1/1981 | Busselet | 417/510 |
| 4,286,637 A | 9/1981 | Wilson | 141/374 |
| 4,296,069 A | 10/1981 | Smith et al. | |
| 4,298,571 A | 11/1981 | DiFulvio et al. | 422/65 |
| 4,346,056 A | 8/1982 | Sakurada | 422/64 |

(Continued)

FOREIGN PATENT DOCUMENTS

EP  0 201 780  11/1986

(Continued)

OTHER PUBLICATIONS

"II Analytical Systems, Discrete Automated Chemistry system with Tableted Reagents" Driscoll et al., Clin. Chem. 29/9, 1983, pp. 1609-1615.

(Continued)

*Primary Examiner*—Jill Warden
*Assistant Examiner*—Jyoti Nagpaul
(74) *Attorney, Agent, or Firm*—Hayes Soloway P.C.

(57) ABSTRACT

Apparatus and methods for automatically staining or treating multiple tissue samples mounted on slides are provided, in which the slides and reagent bottles are held in fixed position, and the reagent and wash solutions brought to the slides.

41 Claims, 11 Drawing Sheets

U.S. PATENT DOCUMENTS

| | | | | |
|---|---|---|---|---|
| 4,358,470 A | 11/1982 | Rasmussen | | 427/4 |
| 4,384,193 A | 5/1983 | Kledzik et al. | | 219/521 |
| 4,406,547 A | 9/1983 | Aihara | | 356/414 |
| 4,430,299 A | 2/1984 | Horne | | 422/64 |
| 4,447,395 A | 5/1984 | Englar et al. | | 422/68 |
| 4,455,280 A | 6/1984 | Shinohara et al. | | 422/63 |
| 4,484,293 A | 11/1984 | Minucciani et al. | | 364/513 |
| 4,528,159 A | 7/1985 | Liston | | 422/65 |
| 4,539,855 A | 9/1985 | Jacobs | | 73/864 |
| 4,543,236 A | 9/1985 | von Gise | | 422/50 |
| 4,577,514 A | 3/1986 | Bradley et al. | | 73/863.01 |
| 4,629,862 A | 12/1986 | Kitagawa et al. | | 219/200 |
| 4,635,791 A | 1/1987 | Jackson et al. | | |
| 4,647,431 A | 3/1987 | Sekine et al. | | 422/63 |
| 4,648,023 A | 3/1987 | Powell | | 364/156 |
| 4,659,971 A | 4/1987 | Suzuki et al. | | 318/568 |
| 4,670,974 A | 6/1987 | Antoszewski et al. | | 29/701 |
| 4,678,752 A | 7/1987 | Thorne et al. | | 435/291 |
| 4,681,741 A | 7/1987 | Hanaway | | 422/100 |
| 4,695,430 A | 9/1987 | Coville et al. | | 422/65 |
| 4,708,886 A | 11/1987 | Nelson | | 422/72 |
| 4,727,409 A | 2/1988 | Conner et al. | | 357/59 |
| 4,727,494 A | 2/1988 | Buote | | 364/513 |
| 4,729,661 A | 3/1988 | Bell | | 356/437 |
| 4,731,335 A | 3/1988 | Brigati | | 436/180 |
| 4,738,824 A | 4/1988 | Takeuchi | | 422/63 |
| 4,764,342 A | 8/1988 | Kelln et al. | | 422/72 |
| 4,774,055 A | 9/1988 | Wakatake et al. | | 422/64 |
| 4,777,020 A | 10/1988 | Brigati | | 422/99 |
| 4,781,891 A | 11/1988 | Galle et al. | | 422/64 |
| 4,795,710 A | 1/1989 | Muszak et al. | | 435/287 |
| 4,798,706 A | 1/1989 | Brigati | | 422/102 |
| 4,801,431 A | 1/1989 | Cuomo et al. | | 422/104 |
| 4,805,469 A | 2/1989 | Commarmot | | 73/864.81 |
| 4,807,152 A | 2/1989 | Lane et al. | | 364/513 |
| 4,815,978 A | 3/1989 | Mazza et al. | | 435/4 |
| 4,835,711 A | 5/1989 | Hutchins et al. | | 364/513 |
| 4,837,159 A | 6/1989 | Yamada | | 436/45 |
| 4,843,566 A | 6/1989 | Gordon et al. | | 364/513 |
| 4,844,868 A | 7/1989 | Rokugawa | | 422/64 |
| 4,847,208 A | 7/1989 | Bogen | | 436/174 |
| 4,852,001 A | 7/1989 | Tsushima et al. | | 364/401 |
| 4,855,109 A | 8/1989 | Muraishi et al. | | 422/63 |
| 4,858,155 A | 8/1989 | Okawa et al. | | 364/557 |
| 4,865,986 A | 9/1989 | Coy et al. | | 435/290 |
| 4,895,706 A | 1/1990 | Root et al. | | 422/102 |
| 4,896,269 A | 1/1990 | Tong | | 364/468 |
| 4,902,481 A | 2/1990 | Clark et al. | | 422/101 |
| 4,919,887 A | 4/1990 | Wakatake | | 422/67 |
| 4,927,765 A | 5/1990 | Saxon et al. | | 436/43 |
| 4,933,146 A | 6/1990 | Meyer et al. | | 422/63 |
| 4,935,875 A | 6/1990 | Shah et al. | | 364/497 |
| 4,961,906 A | 10/1990 | Andersen et al. | | 422/102 |
| 4,964,544 A | 10/1990 | Hanna et al. | | 222/181 |
| 4,965,049 A | 10/1990 | Lillig et al. | | 422/68.1 |
| 4,971,913 A | 11/1990 | Manabe et al. | | 436/55 |
| 4,975,250 A | 12/1990 | Mordecki | | 422/99 |
| 4,979,093 A | 12/1990 | Laine et al. | | 364/167.01 |
| 4,979,128 A | 12/1990 | Seki et al. | | 364/513 |
| 4,985,206 A | 1/1991 | Bowman et al. | | 422/99 |
| 5,002,736 A | 3/1991 | Babbitt et al. | | 422/100 |
| 5,023,187 A | 6/1991 | Koebler et al. | | 436/180 |
| 5,035,866 A | 7/1991 | Wannlund | | 422/102 |
| 5,040,123 A | 8/1991 | Barber et al. | | 364/468 |
| 5,051,238 A | 9/1991 | Umetsu et al. | | 422/64 |
| 5,073,504 A | 12/1991 | Bogen | | 436/174 |
| 5,075,079 A | 12/1991 | Kerr et al. | | |
| 5,084,242 A | 1/1992 | Sakuma et al. | | 422/100 |
| 5,089,229 A | 2/1992 | Heidt et al. | | 422/64 |
| 5,093,557 A | 3/1992 | Lok et al. | | 219/388 |
| 5,096,670 A | 3/1992 | Harris et al. | | 422/65 |
| 5,105,066 A | 4/1992 | Houdy et al. | | 219/385 |
| 5,116,496 A | 5/1992 | Scott | | 210/232 |
| 5,122,342 A | 6/1992 | McCulloch et al. | | 422/65 |
| 5,122,959 A | 6/1992 | Nathanson et al. | | 364/436 |
| 5,148,370 A | 9/1992 | Litt et al. | | 364/468 |
| 5,154,889 A | 10/1992 | Muraishi | | |
| 5,168,453 A | 12/1992 | Nomaru et al. | | 364/468 |
| 5,180,606 A | 1/1993 | Stokes et al. | | 427/2 |
| 5,207,987 A | 5/1993 | Kureshy et al. | | 422/67 |
| 5,213,764 A * | 5/1993 | Kerr et al. | | 422/100 |
| 5,229,074 A | 7/1993 | Heath et al. | | 422/64 |
| 5,231,029 A | 7/1993 | Wootton et al. | | 435/289 |
| 5,232,664 A | 8/1993 | Krawzak et al. | | 422/64 |
| 5,233,533 A | 8/1993 | Edstrom et al. | | 364/468 |
| 5,246,665 A | 9/1993 | Tyranski et al. | | 422/64 |
| 5,273,905 A | 12/1993 | Muller et al. | | 435/301 |
| 5,280,156 A | 1/1994 | Niori et al. | | 219/385 |
| 5,282,149 A | 1/1994 | Grandone et al. | | 364/497 |
| 5,304,347 A | 4/1994 | Mann et al. | | 422/67 |
| 5,311,426 A | 5/1994 | Donohue et al. | | 364/413.09 |
| 5,314,825 A | 5/1994 | Weyrauch et al. | | 436/43 |
| 5,316,452 A | 5/1994 | Bogen et al. | | 417/412 |
| 5,316,726 A | 5/1994 | Babson et al. | | 422/65 |
| 5,334,353 A | 8/1994 | Blattner | | 422/100 |
| 5,352,612 A | 10/1994 | Huber et al. | | 436/47 |
| 5,355,439 A | 10/1994 | Bernstein et al. | | 395/82 |
| 5,355,695 A | 10/1994 | Kawaguchi et al. | | 62/498 |
| 5,356,814 A | 10/1994 | Carrico, Jr. et al. | | 435/286 |
| 5,358,691 A | 10/1994 | Clark et al. | | 422/64 |
| 5,376,313 A | 12/1994 | Kanewske, III et al. | | 264/1.1 |
| 5,402,350 A | 3/1995 | Kline | | 364/468 |
| 5,424,036 A * | 6/1995 | Ushikubo | | 422/64 |
| 5,425,918 A | 6/1995 | Healey et al. | | 422/64 |
| 5,428,470 A | 6/1995 | Labriola, II | | 359/119 |
| 5,431,309 A | 7/1995 | Ophardt | | 222/181.3 |
| 5,439,645 A | 8/1995 | Saralegui et al. | | 422/64 |
| 5,439,649 A | 8/1995 | Tseung et al. | | 422/99 |
| 5,446,652 A | 8/1995 | Peterson et al. | | 364/578 |
| 5,475,610 A | 12/1995 | Atwood et al. | | 364/500 |
| 5,479,581 A | 12/1995 | Kleinschnitz | | 395/82 |
| 5,496,518 A | 3/1996 | Arai et al. | | |
| 5,512,248 A | 4/1996 | Van | | 422/100 |
| 5,523,056 A | 6/1996 | Miller | | 422/64 |
| 5,525,302 A | 6/1996 | Astle | | 422/100 |
| 5,525,515 A | 6/1996 | Blattner | | 436/49 |
| 5,575,976 A | 11/1996 | Choperena et al. | | 422/64 |
| 5,576,215 A | 11/1996 | Burns et al. | | 436/50 |
| 5,578,455 A | 11/1996 | Tosa et al. | | 435/7.32 |
| 5,589,649 A | 12/1996 | Brinker et al. | | |
| 5,595,707 A * | 1/1997 | Copeland et al. | | 422/64 |
| 5,597,733 A * | 1/1997 | Bell et al. | | 436/54 |
| 5,601,141 A | 2/1997 | Gordon et al. | | 165/263 |
| 5,629,201 A | 5/1997 | Nugteren et al. | | 435/283.1 |
| 5,639,665 A | 6/1997 | Arai et al. | | 436/50 |
| 5,645,114 A | 7/1997 | Bogen et al. | | 141/145 |
| 5,645,144 A | 7/1997 | Bogen et al. | | 141/145 |
| 5,646,046 A | 7/1997 | Fischer et al. | | 436/49 |
| 5,646,049 A | 7/1997 | Tayi | | 436/518 |
| 5,650,327 A | 7/1997 | Copeland et al. | | 436/46 |
| 5,654,199 A | 8/1997 | Copeland et al. | | 436/46 |
| 5,654,200 A | 8/1997 | Copeland et al. | | 436/46 |
| 5,656,493 A | 8/1997 | Mullis et al. | | 435/286.1 |
| 5,695,718 A | 12/1997 | Imai et al. | | 422/62 |
| 5,736,105 A | 4/1998 | Astle | | 422/100 |
| 5,737,498 A | 4/1998 | Murray | | 395/81 |
| 5,819,842 A | 10/1998 | Potter et al. | | 165/206 |
| 5,839,091 A | 11/1998 | Rhett et al. | | |
| 5,861,094 A | 1/1999 | Goehde | | 210/232 |
| 5,875,286 A | 2/1999 | Bernstein et al. | | 395/82 |
| 5,879,944 A | 3/1999 | Komatsu | | 436/50 |
| 5,909,674 A | 6/1999 | Schaffer et al. | | 706/13 |
| 5,947,167 A | 9/1999 | Bogen et al. | | 141/1 |
| 5,948,359 A | 9/1999 | Kalra et al. | | 422/65 |

| | | | | |
|---|---|---|---|---|
| 5,975,740 | A | 11/1999 | Lin et al. | 364/468.05 |
| 5,985,672 | A | 11/1999 | Kegelman et al. | 436/50 |
| 6,054,099 | A | 4/2000 | Levy | 422/102 |
| 6,068,393 | A | 5/2000 | Hutchins et al. | 364/468.19 |
| 6,092,695 | A | 7/2000 | Loeffler | |
| 6,093,574 | A | 7/2000 | Druyor-Sanchez et al. | 436/180 |
| 6,096,271 | A | 8/2000 | Bogen et al. | 422/64 |
| 6,180,060 | B1 | 1/2001 | Green et al. | 422/64 |
| 6,180,061 | B1 | 1/2001 | Bogen et al. | |
| 6,183,645 | B1 | 2/2001 | DeWitt | 210/634 |
| 6,183,693 | B1 | 2/2001 | Bogen et al. | 422/64 |
| 6,192,945 | B1 | 2/2001 | Ford et al. | 141/2 |
| 6,193,933 | B1 | 2/2001 | Sasaki et al. | 422/64 |
| 6,241,947 | B1 | 6/2001 | Komatsu et al. | 422/67 |
| 6,296,764 | B1 | 10/2001 | Guirguis et al. | 210/323.1 |
| 6,296,809 | B1 * | 10/2001 | Richards et al. | 422/64 |
| 6,352,861 | B1 | 3/2002 | Copeland et al. | 436/46 |
| 6,372,144 | B1 | 4/2002 | Vassarotti | 210/650 |
| 6,495,106 | B1 | 12/2002 | Kalra et al. | |
| 6,531,094 | B2 | 3/2003 | Seto et al. | 422/64 |
| 6,537,818 | B2 | 3/2003 | Richards et al. | 436/54 |
| 6,541,261 | B1 * | 4/2003 | Bogen et al. | 436/46 |
| 6,582,962 | B1 | 6/2003 | Richards et al. | |
| 6,594,537 | B1 | 7/2003 | Bernstein et al. | 700/100 |
| 6,673,620 | B1 | 1/2004 | Loeffler et al. | |
| 6,783,733 | B2 | 8/2004 | Bogen et al. | |
| 6,827,900 | B2 | 12/2004 | Thiem et al. | |
| 2001/0004449 | A1 | 6/2001 | Suzuki et al. | 422/100 |
| 2001/0016358 | A1 | 8/2001 | Osawa et al. | 436/180 |
| 2001/0055545 | A1 | 12/2001 | Takii et al. | 422/100 |
| 2002/0037239 | A1 | 3/2002 | Komatsu | 422/100 |
| 2002/0054830 | A1 | 5/2002 | Bogen et al. | |
| 2003/0032191 | A1 | 2/2003 | Hilson et al. | 436/47 |
| 2003/0203493 | A1 * | 10/2003 | Lemme et al. | 436/46 |
| 2004/0191128 | A1 | 9/2004 | Bogen et al. | |
| 2004/0241050 | A1 | 12/2004 | Bogen et al. | |

FOREIGN PATENT DOCUMENTS

| | | |
|---|---|---|
| EP | 0 240 134 | 2/1987 |
| EP | 0517835 | 2/1996 |
| EP | 1 052 497 A2 | 11/2000 |
| EP | 1 052 497 A3 | 1/2003 |
| FR | 2 239 167 | 1/1967 |
| FR | 2 528 122 | 4/1982 |
| GB | 2143205 | 2/1985 |
| GB | 2 216 259 | 10/1989 |
| JP | 55-107957 | 2/1979 |
| JP | 55-014157 | 3/1980 |
| JP | 63-208761 | 8/1988 |
| JP | 04-356845 | 12/1992 |
| WO | WO87/00086 | 1/1987 |
| WO | WO88/02865 | 4/1988 |
| WO | WO91/13335 | 9/1991 |
| WO | WO93/07486 | 5/1993 |
| WO | PCT/US98/16604 | 12/1998 |
| WO | WO99/43434 | 9/1999 |

OTHER PUBLICATIONS

"Concurrent HPLC Analyses of Carbohydrate Distribution and 5-(Hydroxymethyl)-2-Furaldehyde Usign Robotics" Mueller et al., *Journal of Chromatographic Science*, vol. 25, 1987, pp. 198-201.

"An automated device for immunocytochemistry" Stark et al., *Journal of Immunological Methods*, 107 (1998) 89-92.

"Automation of APAAP immunocytochemical technique" Stross et al., *J Clin Pathol*, 42 (1989) 106-112.

"Automation of In situ Hybridization: Application of the Capillary Action Robotic Workstation" Unger et al., *The Journal of Histotechnology*, vol. 11 No. 4 (1988) 253-258.

"Robotics for the Bioanalytical Laboratory-A Flexible System for the analysis of Drugs in Biological Fluids" Fouda et al., *Trac Trends in Analytical Chemistry*, 10 pgs.

"The SimKit Sytem: Knowledge-Based Simulation and Modeling Tools in KEE" Stelzner et al., An Intellicorp Technical Article, 1987, 22 pgs.

"Immunocytochemistry if Automated: Development of A Robotic Worksation Based Upon the Capillary Action Principle" Brigati et al., *The Journal of Histotechnology*, vol. 11, No. 3, 1988, pp. 165-183.

"Anatomic Viral Detection Is Automated: The Application of a Robotic Molecular Pathology System for the Detection of DNA Viruses in Anatomic Pathology Substrates, Using Immunocytochemical and Nucleic Acid Hybridization Techniques" Montone et al., *The Yale Journal of Biology and Medicine*, 62, 1989, pp. 141-158.

"Viral Diagnosis by in situ Hybridization, Description of a Rapid Simplified Colorimetric Method" Unger et al., *The American Journal of Surgical Pahtology*, 10(1), 1986, pp. 1-8.

"Colorimetric In-Situ Hybridization in Clinical Virology: Development of Automated Technology" Unger et al., *Current Topics in Microbiology and Immunology*, vol. 143, 1989, pp. 21-31.

"Laboratory Robotics and Arificial Intelligence" Isenhour et al., *Clinical Chemistry*, 36/9, 1990, pp. 1561-1566.

"Intelligent Robots-The Next Step in Laboratory Automation" Isenhour et al., *Analytical Chemistry*, vol. 61, No. 13, 1989, pp. 805-814.

"TORTS: An Expert System for Temporal Optimization of Robotic Procedures" Isenhour et al., *Journal of Chemical Information and Computer Sciences*, No. 28, 1988, pp. 215-221.

"Robotics in the Laboratory" Isenhour, *Journal of Chemical Information and Computer Sciences*, No. 25, 1985, pp. 292-295.

"Robot Task Planning System Based on Product Modeling" Kawaba et al., pp. 471-476.

"Robotic Work Station for Microscale Synthetic Chemistry: On-Line Absorptior Spectroscopy, Quantitative Automated Thin-Layer Chromatography, and Multiple Reactions in Parallel" Lindsey et al., *Rev. Sci. Instrum.*, 59(6), 1988, pp. 940-950.

"Job Sequencing with Fuzzsy Processing Times" McCahon et al., *An International Journal Computers & Mathematics with Applications*, vol. 19, No. 7, 1990, pp. 31-41.

"Scheduling Project Networks with Resource Constraints and Time Windows" Bartusch et al., *Annals of Operations Research*, 16, 1988, pp. 201-140.

"Basic Structure of Computers" Hamacher et al., *Computer Organization Second Edition*, pp. 1-14.

"A Guide to GUIs" Hayes et al., *Byte*, 1989, pp. 250-257.

"Robot Simulator in Tips/Geometric Simulator" Okino et al., *Robotics and Computer Integrated Manufacturing*, vol. 3, No. 4, 1987, pp. 429-437.

"Robot Task Planning: Programming Using Interactive Computer Graphics" Sjolund et al, pp. 7-122-7-135.

"Time Window Constrained Routing and Scheduling Problems" Solomon et al., *Transportation Science*, vol. 22, No. 1, 1988, pp. 1-13.

"The Abbott 1Mx Automated Benchtop Immunochemistry Analyzer System" Flore et al., Clin. Chem. 34/9, 1988, pp. 1726-1732.

"Early Development of the Modern Robot" *Critchlow, Introduction to Robotics*, Chapter 2, pp. 37-56, Chapter 6, pp. 151-213.

"An Automated Device for Immunocytochemistry" Stark et al., Journal of Innumological Methods, 107, 1988, pp. 89-92.

"Automated Immunochemistry" Ma Whinney et al., *Journal Clin Pathol*. 1990, pp. 591-596.

"Automation of APAAP Immunocytochemical Technique" Stross et al., *Journal Clin. Pathol.*, No. 42, 1989, pp. 106-112.

Mewburn Ellis letter to EPO including revised set of claims for EPO Appl. No. 91906210.9.

German List "Anlage K5" Merkmalsgliederung Anspruch 1.

"DNA Sequencing with Thermus Aquaticus DNA Polymerase and Direct Sequencing of Polymerase Chain Reaction-Amplified DNA" Innis et al., *Proc. Natl. Acad. Sci. USA* , No. 85, 1988, pp. 9436-9440.

"Enzymatic Amplification of B-Globin Genomic Sequences and Restriction Site Analysis for Diagnosis of Sickle Cell Anemia" Saiki et al., Science vol. 230, 1985, pp. 1350-1354.

File History of 488601 in German, 2 pgs.

"The Complete Immunoperoxidase System," IMMULOK, advertisement, 1 pg.

United Stated Court of Appeal for *The Federal Court, Cytologix Corporation* v. *Ventana Medical Systems, Inc.,* Case No. 04-1446, Decision decided Sep. 21, 2005, p. 1-18.

* cited by examiner

AUTOMATED MOLECULAR PATHOLOGY APPARATUS HAVING FIXED SLIDE PLATFORMS

CROSS REFERENCE TO RELATED APPLICATIONS

This application claims priority for U.S. Provisional Application Ser. No. 60/350,273, filed Nov. 2, 2001.

FIELD OF THE INVENTION

The present invention is directed to apparatus for use in diagnostic molecular pathology and, more particularly, to such apparatus used for the automated staining and/or treating of tissue samples mounted on microscope slides.

BACKGROUND OF THE INVENTION

Molecular pathology is the examination at a molecular level of the DNA, mRNA, and proteins that cause or are otherwise associated with disease. From this examination important information about patient diagnosis, prognosis, and treatment options can be elucidated. The practice of molecular pathology is generally divided into two main areas: (i) analysis of DNA, mRNA, and proteins in intact cells (in-situ), and (ii) analysis of these biological materials after they have been extracted from tissues. The first category, to which the present invention is primarily directed, has the advantage that it allows the pathologist or scientist to study the histopathologic architecture or morphology of the tissue specimen under the microscope at the same time that the nucleic acid or proteins are being assayed. These techniques include immunohistochemistry (IHC) which looks at proteins, in-situ hybridization (ISH) which looks at nucleic acids, histochemistry (HC) which looks at carbohydrates, and enzyme histochemistry (EHC) which looks at enzyme chemistry. For example, ISH can be used to look for the presence of a genetic abnormality or condition such as amplification of cancer causing genes specifically in cells that, when viewed under a microscope, morphologically appear to be malignant. ISH is also useful in the diagnosis of infectious diseases as it allows detection not only of a microbial sequence but also of precisely which cells are infected. This may have important clinicopathologic implications and is an effective means to rule out the possibility that positive hybridization signal may have come from an adjacent tissue of no clinical concern or from blood or outside contamination.

IHC utilizes antibodies which bind specifically with unique epitopes present only in certain types of diseased cellular tissue. IHC requires a series of treatment steps conducted on a tissue section or cells (e.g. blood or bone marrow) mounted on a glass slide to highlight by selective staining certain morphological indicators of disease states. Typical steps include pretreatment of the tissue section to remove the paraffin and reduce non-specific binding, retrieval of antigens masked by cross-linking of the proteins from the chemical fixatives, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Most of these steps are separated by multiple rinse steps to remove unreacted residual reagent from the prior step. Incubations can be conducted at elevated temperatures, usually around 37° C., and the tissue must be continuously protected from dehydration. ISH analysis, which relies upon the specific binding affinity of probes with unique or repetitive nucleotide sequences from the cells of tissue samples or bodily fluids, requires a similar series of process steps with many different reagents and is further complicated by varying temperature requirements.

In view of the large number of repetitive treatment steps needed for both IHC and ISH, automated systems have been introduced to reduce human labor and the costs and error rate associated therewith, and to introduce uniformity. Examples of automated systems that have been successfully employed include the ES®, NexES®, DISCOVERY™, BENCHMARK™ and Gen II® staining Systems available from Ventana Medical Systems (Tucson, Ariz.). These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

Instrumentation such as the Ventana Medical Systems ES®, NexES®, BENCHMARK® and DISCOVERY® systems are fundamentally designed to sequentially apply reagents to tissue sections mounted on one by three inch glass microscope slides under controlled environmental conditions. The instrument must perform several basic functions such as reagent application, washing (to remove a previously applied reagent), jet draining (a technique to reduce the residual buffer volume on a slide subsequent to washing), Liquid Coverslip™ application (a light oil application used to contain reagents and prevent evaporation), and other instrument functions.

The Ventana Medical Systems staining instruments mentioned above process slides on a rotating carousel. The instrumentation described herein has the slides fixed in a stationary position and rotates the basic processing stations above the fixed slides. The following details of how the slides are processed, the process algorithm, is the same regardless of the physical configuration.

The process of staining tissue on a slide consists of the sequential repetition of the basic instrument functions described above. Essentially a reagent is applied to the tissue then incubated for a specified time at a specific temperature. When the incubation time is completed the reagent is washed off the slide and the next reagent is applied, incubated, and washed off, etc, until all of the reagents have been applied and the staining process is complete.

It is desirable to permit any staining protocol for any of the slides being run, i.e. any combination of reagents and incubation times. In addition, to stain multiple slides as quickly as possible the instrument should process the slides simultaneously. This is feasible given that most of the time slides are just incubating, thus freeing up time to perform the washing, reagent application and other functions on other slides.

One algorithm to accomplish simultaneous staining (sometimes referred to as the "random access" method) is to create a task and time schedule for each slide in the run, then perform each task on each slide when the schedule calls for it. The problem with this method is that incubation times will not be accurate if the instrument is busy performing a task on one slide when it is time to be washing another slide (thereby completing incubation on that slide). The variation in incubation times will be unpredictable since the total number of slides and the slide protocols vary.

Slide processing using the lock step algorithm insures that all incubation times are accurate and predictable irrespective of the number of slides processed or the variation in slide protocols. While incubation times are assured, the lock step algorithm implies that incubation times must be an increment of the fundamental incubation time period. In the above example the incubation period is two minutes, therefore total incubation times must be two, four, six, eight etc. minutes in duration. However, the preferred embodiment of the present invention uses a four minute incubation time. Generally this is not a particular limitation since typical incubation times are an order of magnitude longer than the fundamental incubation period.

Prior art staining systems typically include either convection or radiation to warm the samples above laboratory ambient temperatures for steps requiring elevated temperatures. Heating the slide improves staining quality by acceleration of the chemical reaction and can permit a reaction temperature more closely matching body temperature (about 37° C.) at which antibodies are designed to react. While such convection or radiant heating systems have been generally suitable for IHC, which is antibody based, they are less suitable for ISH, which is nucleic acid based and requires higher and more precise temperature control. In order to denature the DNA double helix of both the target sample and the probe so as to render them single stranded, the temperature must be raised above the melting point of the duplex, usually about 94° C. Precise temperature control is also required in ISH to effect probe hybridization at the desired stringency. The selected temperature must be low enough to enable hybridization between probe and target, but high enough to prevent mismatched hybrids from forming.

Hot air convection, conduction or radiant heat heating units typically employed with prior art automated tissue stainers do not permit the temperature of individual slides to be separately controlled. With prior art systems all of the slides are heated to the same temperature at any given time during the process. For example, U.S. Pat. No. 5,645,114 to Bogen et al. discloses a dispensing assembly adapted to carry a plurality of microscope slides. Individual slide holders containing resistive heating units are provided. However, with the assembly taught by Bogen et al., all of the slides would be heated to a common temperature because no means are disclosed for separate heating controls or for shielding slides from heat generated by adjacent slides.

Other difficulties frequently encountered in both IHC and ISH testing results from the manner in which the tissues are typically preserved. The mainstay of the diagnostic pathology laboratory has been for many decades the formalin-fixed, paraffin embedded block of tissue, sectioned and mounted upon glass slides. Fixation in such a preservative causes cross-linking of macromolecules, both amino acids and nucleic acids. These cross-linked components must be removed to allow access of the probe to the target nucleic acid and to allow the antibody to recognize the corresponding antigen. "Unmasking" the antigen and/or nucleic acid is typically accomplished manually with multiple pretreatment, protolytic digestion, and wash steps.

Prior to staining, complete removal of the paraffin is also required so that it does not interfere with antibody or probe binding. Deparaffinization normally is achieved by the use of two or three successive clearing reagents that are paraffin solvents such as xylene, xylene substitutes or toluene.

The foregoing discussion of the prior art largely derives from Richards et al. U.S. Pat. No. 6,296,809, assigned to Ventana Medical Systems, in which there is described apparatus and methods for automatically staining or treating multiple tissue samples mounted on microscope slides so that each sample can receive an individualized staining or treatment protocol even when such protocols require different temperature parameters. More specifically, there is described in the '809 patent apparatus comprising a computer controlled, bar code driven, staining instrument that automatically applies chemical and biological reagents to tissue or cells mounted or affixed to standard glass microscope slides. According to the '809 patent, a plurality of slides are mounted in a circular array on a carousel which rotates, as directed by the computer, to a dispensing location placing each slide under one of a series of reagent dispensers on a second rotating carousel positioned above the slides. Each slide receives the selected reagents (e.g. DNA probe) and is washed, mixed and/or heated in an optimum sequence and for the required period of time.

According to the '809 patent, individual slides are carried on thermal platforms radially mounted to the carousel. Sensors also mounted to the slide carousel, individually monitor and control each thermal platform separately. Apparatus made in accordance with the '809 patent is available commercially from Ventana Medical Systems, of Tucson, Ariz. as the DISCOVERY™ or BENCHMARK™ systems.

The present invention is a modification and improvement over the prior art including the apparatus and methods described in the '809 patent. More particularly, the present invention rather than bringing the slides to the reagent, stain, and wash stations, brings the reagent, stain and wash stations to fixedly positioned slides. That is to say, in the present invention the slides are fixedly positioned in the apparatus, and the various washing, staining and reagent fluids selectively delivered to the slides. Fixing the slides in position in the apparatus eliminates expensive and disposable dispensers, and simplifies wiring to the heaters, and also eliminates the potential that a slide may be dislocated by rapid start and stop movement of the slide carousel, which, in a worst case scenario could result in a domino or train-wreck effect where one dislocated slide hits the neighboring slide causing that slide to dislocate, and so forth. Additionally, maintaining the slides in fixed position eliminates inertial problems of a high-volume reagent and slide carousel. Thus, motors and bearings need not be so robust.

Further features and advantages of the present invention will be seen from the following detailed description, taken in conjunction with the accompanying drawings, wherein like numerals depict like parts, and wherein:

DETAILED DESCRIPTION OF THE INVENTION

Figure 1:
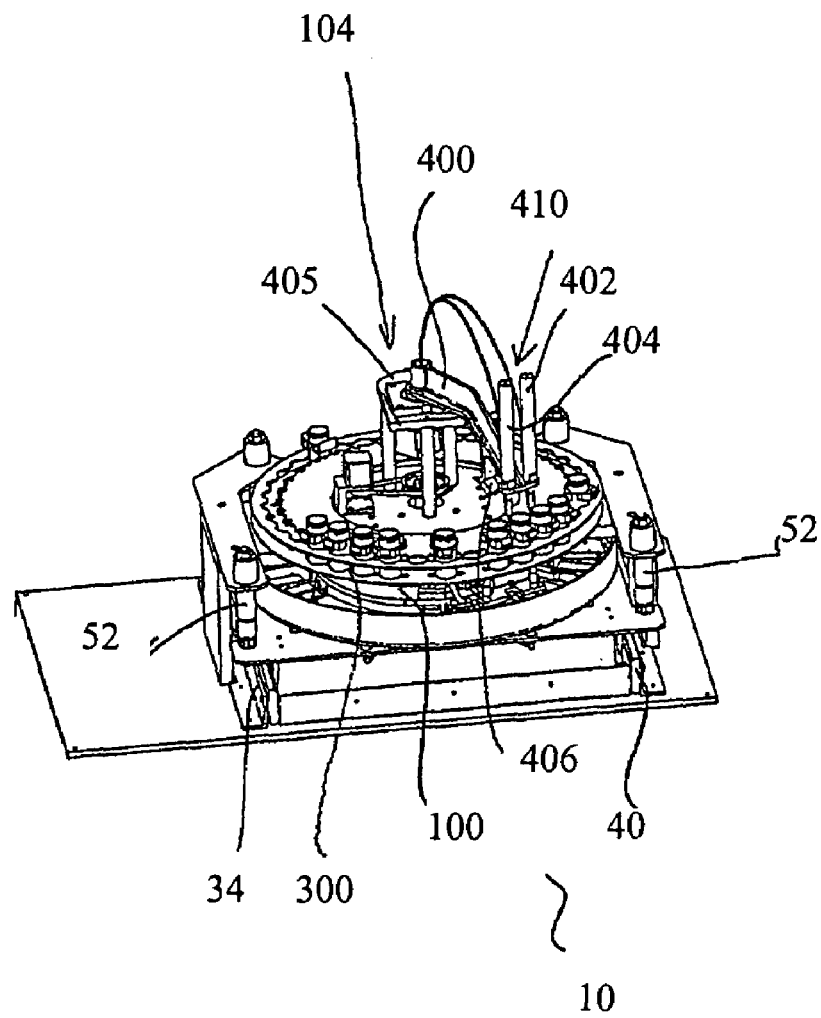
FIG. 1 is a perspective view of the apparatus of the present invention shown with the slide cabinet shell removed.

Referring now in detail to the drawings wherein like parts are designated by like reference numerals throughout, there is illustrated in FIG. 1 a perspective view of the molecular pathology apparatus according to the present invention which is designated generally by reference numeral 10. For the purposes of clarity, several of the reagent bottles, as well as the cabinet shell, and liquid and air supply tubing and electrical wiring are omitted from the drawings. Apparatus 10 is designed to automatically stain or otherwise treat tissue mounted on microscope slides with nucleic acid probes, antibodies, and/or other reagents in a desired sequence, time and temperature. Tissue sections so stained or treated are then to be viewed under a microscope by a medical practitioner who reads the slide for purposes of patient diagnosis, prognosis, or treatment selection.

Figure 2:
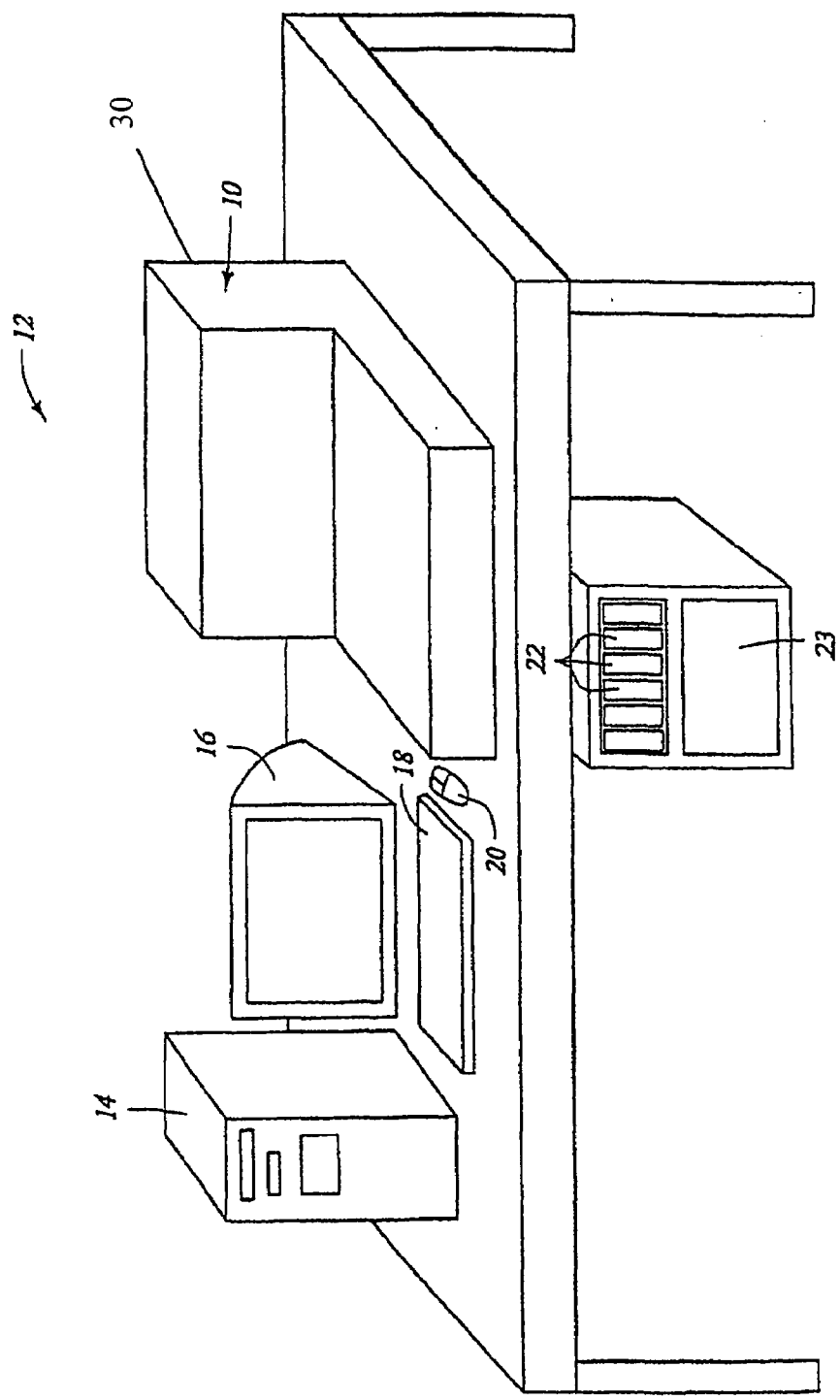
FIG. 2 is a perspective view of the apparatus of the present invention shown in conjunction with a computer and other instruments with which it operates.

In a preferred embodiment, apparatus 10 functions as one component or module of a system 12 (FIG. 2) which also comprises a host computer 14 preferably a personal computer, monitor 16, keyboard 18, mouse 20, bulk fluid containers 22, waste container 23 and related equipment. Additional staining modules or other instruments may be added to system 12 to form a network with computer 14 functioning as a server. Alternatively, some or all of these separate components could be incorporated into apparatus 10 making it a stand-alone instrument. Referring also to FIGS. 3-7, as set forth in greater detail below, a plurality of slide platforms 50 are mounted radially about a center point 32 of drawer 34 upon which standard glass slides 60 with tissue samples may be placed. Drawer 34 is preferably constructed of stainless steel and is slidably mounted in housing 30 on rails 40 or the like. The temperature of each slide may be individually controlled by means of sensors and a microprocessor, i.e. as taught in the above-mentioned '809 patent.

Each of the slide platforms 50 is connected through individual wires and a wiring harness (not shown) to a microprocessor. A feature and advantage of the present invention which results from fixedly mounting the slide platforms in drawer 34 is that each of the heaters and thermal sensors may be hardwired thereby eliminating the need for a slip ring assembly or rotor couplings, as well as complex stepping motors, etc. for locating and positioning a rotating slide carousel as required in prior art devices. Also, the possibility that a slide or slides may be shifted or dislocated during rapid start and stop rotation of the slide carousel is eliminated.

In a particularly preferred embodiment, a plurality of slots or channels are formed on the top surface of each of the slide heaters, i.e. the interface surface between the slide heater and the slide, for gathering and venting gas bubbles as may form during heating, i.e. in accordance with co-pending U.S. application Ser. No. 09/953,417, filed Sep. 11, 2001, and assigned to the common assignee, which disclosure is incorporated herein by reference.

Referring also to FIGS. 1, 2, 5 and 6, drawer 34 includes a circular pan 35 having a peripheral wall 36 serving as a splash guard, a peripheral trough 37 and a central drain 38, i.e. at center point 32, both connected to drain lines (39) which in turn are connected to waste container 23. Drawer 34 is slidably mounted in housing 30 on rails 40. Rails 40, in a preferred embodiment, comprise three piece telescoping rails so that the drawer 34 may be slid clear of housing 30 to permit access to all of the slide platforms 50 for slide loading and removal. A damping means 42 such as a pneumatic means, electromotive means, mechanical spring damper or the like preferably is provided to smooth movement of the drawer whereby to avoid possible dislodging of slides, particularly when the drawer is closed. Also, in a preferred embodiment of the invention, rails 40 are supported on a lift mechanism such as pneumatic cylinders 52 (see FIG. 1), which automatically index to permit the rails 40 to move up and down so that the drawer 34 may be dropped to permit wall 36 to clear the nozzle plate 100 when the drawer is slid in and out of the apparatus.

Slide drawer 34 is divided into thirty-five equal pie-shaped sections 70. Thirty of the pie-shaped sections 70 are occupied by slide platforms 50 while the five remaining pie-shaped sections 70A (FIG. 4) at the rear of the drawer are devoid of slide platforms 50. In other words, a row of thirty slide platforms 50 are radially mounted on drawer 34 and evenly spaced from one another, except at the ends of the row.

However, the invention is not limited to thirty active slide locations, and more or fewer slide locations may be employed. An alternative embodiment may be implemented by aligning the platforms 50 linearly, which results in potentially limitless number of platforms.

Figure 3:
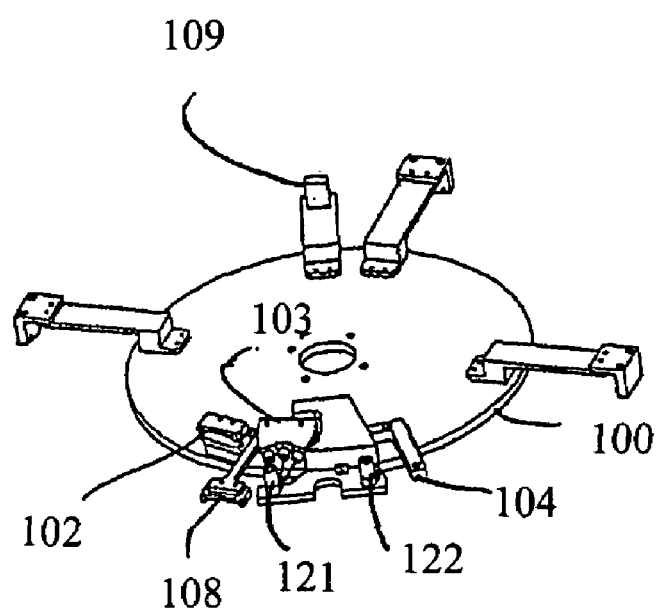
FIG. 3 is a perspective view and FIG. 3a is an exploded view of details of the nozzle plate portion of the present invention.
Figure 3A:
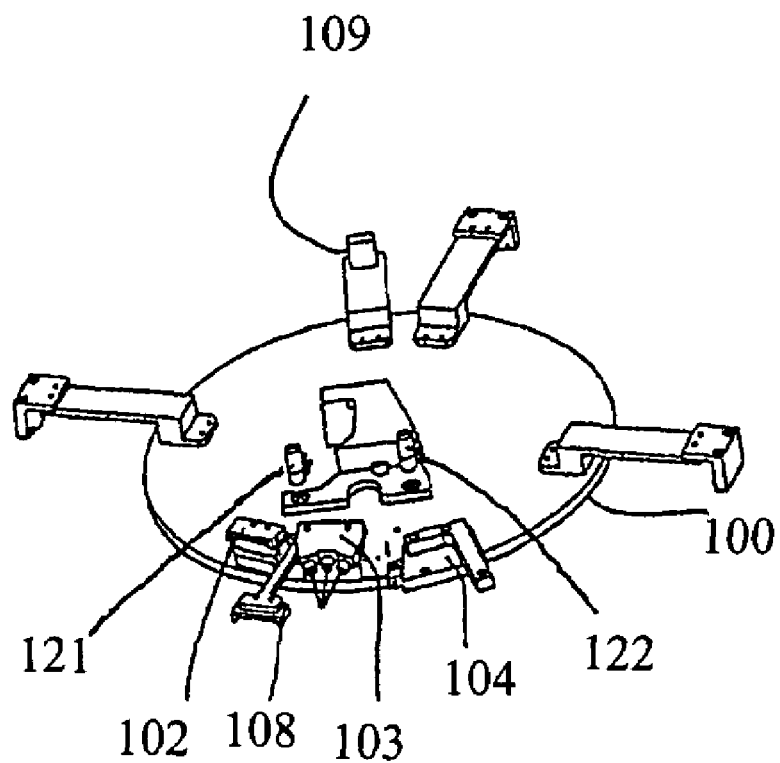
Figure 4:
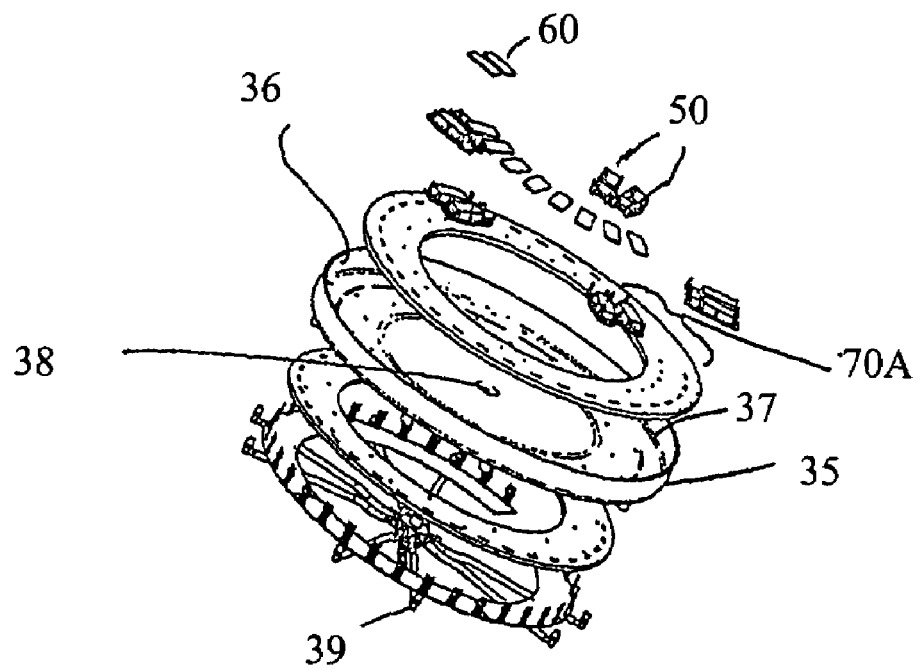
FIG. 4 is an exploded view of details of the slide plate portion of the present invention.
Figures 5, 6:
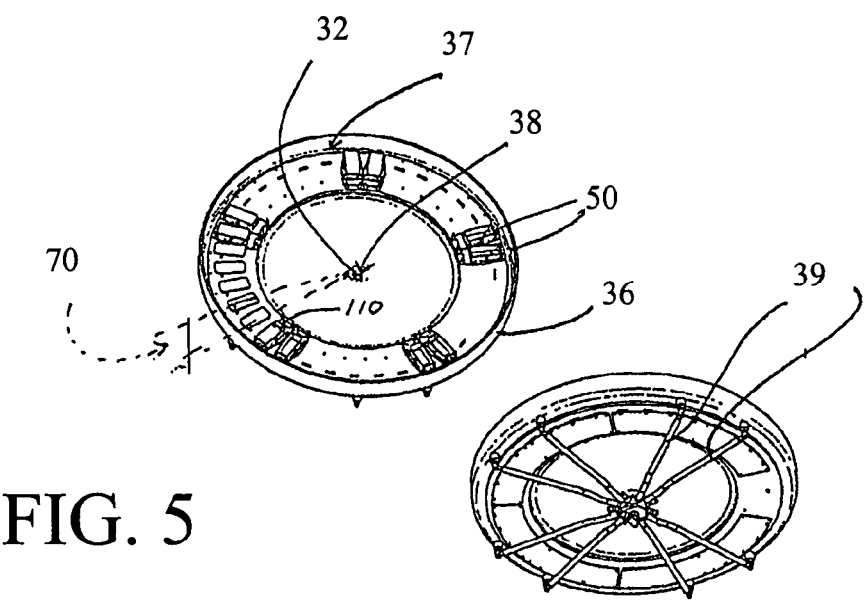
FIGS. 5 and 6 are perspective views, from the top and the bottom, respectively, of portions of the slide plate portion of the present invention.
Figure 7:
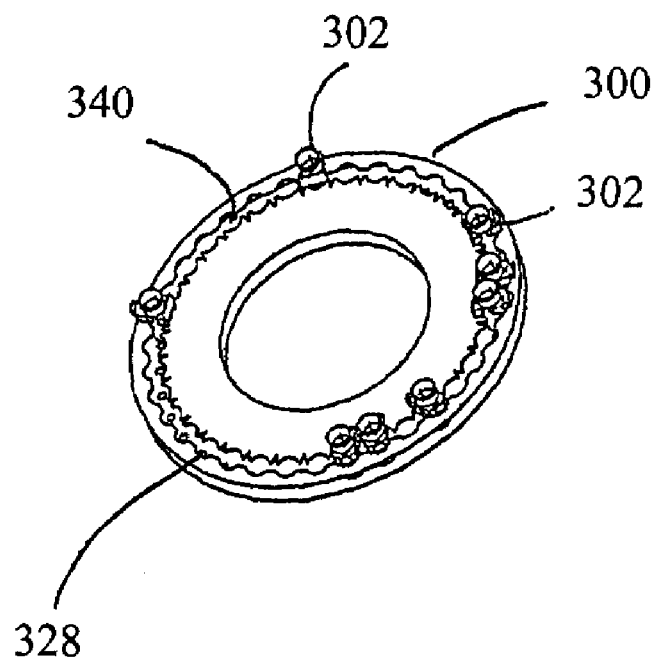
FIG. 7 is a perspective view of the reagent plate portion of the present invention.

Referring to FIGS. 1 and 3, a nozzle plate 100 is concentrically and rotatably mounted above slide drawer 34. Nozzle plate 100 is mounted on a shaft (not shown) supported by a bridge 110, and driven by a computer controlled stepping motor and drive belt (not shown), and rotates 185° plus or minus from a home position 104 at the rear of the drawer. The computer controlled stepper motor and drive belt are conventional in this art. Accordingly, details are omitted for the sake of clarity.

Nozzle plate 100 carries the various slide treatment stations, other than the reagent dispensing station. Thus, nozzle plate 100 carries dual rinse nozzle block 102, volume adjust/stringency block 103, Liquid Coverslip™ evaporation inhibitor liquid application block 104, vortex mixer air jet block 106, jet drain knives 108, and the like, all for preparing a slide for staining, stain removal, and the like, and to clear bar codes 110 carried on the slides, and a bar code reader 109, all as described in detail in U.S. Pat. No. 5,654,200 to Copeland et al., which disclosure is incorporated herein by reference. In other words, nozzle plate 100 carries all of the functions for slide preparation, cleaning, reagent mixing, Liquid Coverslip™ application, etc. other than reagent application, as described in the '200 patent to Copeland et al., plus wash stations 121, 122 for the reagent application probes as will be described in detail below.

Preferably, but not necessarily, the various rinse nozzle blocks, vortex mixer air jet blocks, air knives, etc. are arranged adjacent to one another so that the nozzle plate may be indexed and advanced in a "lock-step" manner to sequentially treat a slide according to an accepted protocol. For example, air knives 108 may be arranged immediately adjacent rinse nozzle blocks 106 so that nozzle plate 100 may be advanced in "lock step" manner past a selected slide, and the slide rinsed and fluid stripped, etc. Also, if desired, vortex mixer air jet blocks 106 may be oriented to impinge simultaneously on two adjacent slides.

For the sake of clarity, fluid and air supply tubing for the several slide treatment stations have been omitted from the drawings. It will be understood, however, that the fluid and air supply tubing are made long enough to permit 185° rotation of the valve plate so that each slide treatment station can reach each slide 60. A pair of wash stations 121, 122 spaced two thirty-fifths of a revolution (approximately 20.572°) apart as will be described in detail hereinafter, are also attached to and radially extend beyond the periphery of the nozzle plate 100, and rotate with the nozzle plate 100.

Reagent plate 300 is fixedly mounted to arch 110 vertically above nozzle plate 100, which arch in turn is fixedly mounted within housing 30. A plurality of reagent bottles 302 are removably mounted within recesses 304 formed equally spaced adjacent the periphery of reagent plate 300. In the illustrated embodiment, a total of thirty-five reagent bottles are mounted on the reagent plate, spaced approximately one thirty-fifth (approximately 10.286°) apart.

The reagents may include any chemical or biological material conventionally applied to slides including nucleic acid probes or primers, polymerase, primary and secondary antibodies, digestion enzymes, pre-fixatives, post-fixatives, readout chemistry, counterstains, and the like.

Figure 8:
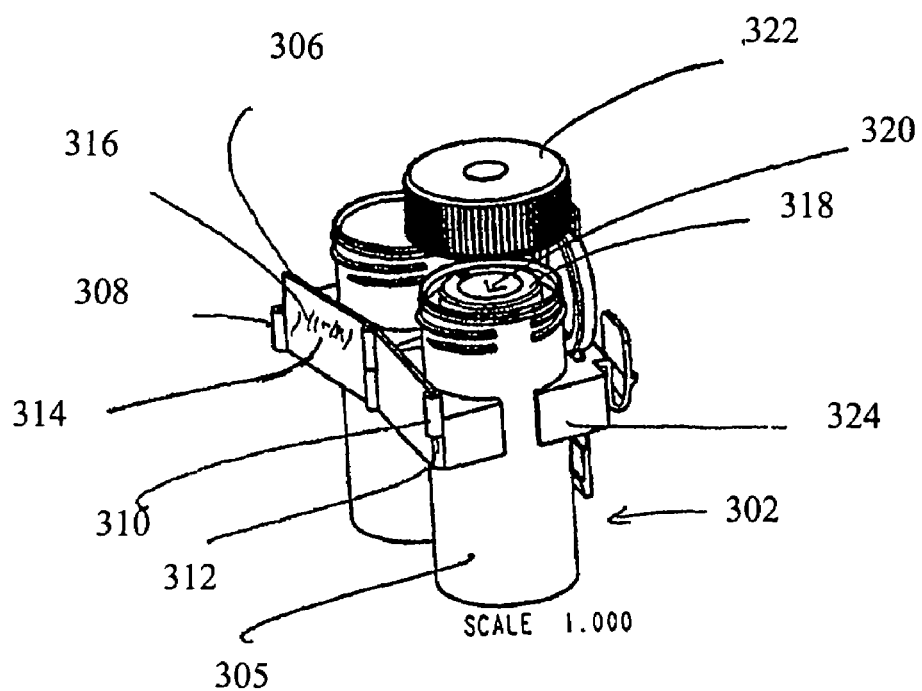
FIG. 8 is a perspective view showing two reagent bottles of the present invention.

Referring also to FIG. 8, the reagent bottles 302 each comprise a cylindrical hollow body 305 closed at the bottom end by an integrally formed bottom wall (not shown). Each bottle 302 includes an integrally formed bracket 306 which serves to maintain the bottles 304 at a desired height in reagent plate 300, and which serves also to permit the stringing together of a plurality of like bottles 302. Accordingly, each bracket 302 includes a hinge element 308 for cooperating with a hinge element 310 of an adjacent bottle 302. In the illustrated embodiment, hinge elements 308 and 310 are shown as conventional pin-hinges in which the upper hinge 308 includes a pin 312 which fits into the lower hinge 310, i.e. similar to a conventional door hinge. However, bottles 302 may be hinged together in a variety of ways.

Bracket 306 preferably includes a flat surface 314 upon which is carried a bar code 316 for identifying the contents of the bottle 302. Bottles 302 also include an insert 318 having a tapered top surface 320 fitted in the top end of the bottles for locating a reagent transfer probe as will be described in detail hereinafter, and a cap 322 which may be either twist or snap-fitted to the bottle 302 for sealing the bottle 302.

Making brackets 306 attachable to one another permits a lab worker to assemble a chain of reagents for use, and also to remove the chain of reagents so that the reagents may be refrigerated, for example, overnight when not in use.

Figure 9:
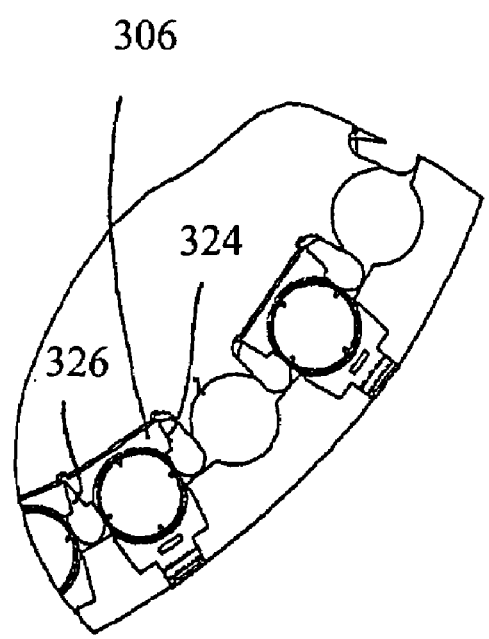
FIG. 9 is a top plan view of two reagent bottles of the present invention.

Referring next to FIG. 9, the side walls 324 of brackets 306 are tapered so that a pie-shaped space 326 is formed between two bottles when two bottles are fastened together in a string, and mounted in recesses 104 in the reagent plate 300, thereby exposing holes 328 formed through reagent plate 300. Holes 328 are formed in the same concentric circle as recesses 304, and are spaced equidistant between adjacent recesses 304. The purpose of pie-shaped spaces 326 and holes 328 is to provide clearance for reagent transfer probes 402, 404 as will be described in detail below.

Referring again to FIG. 1, an arm 400 is rotatably mounted on arch 405 concentrically above reagent plate 300, and carries a pair of reagent transfer probes 402, 404 located at the distal end of arm 400 and spaced approximately 10.286° apart. Arm 400 also carries a bar code reader 406 for reading bar codes 316 on the reagent bottles. Arm 400 is rotatably driven by a computer driven stepping motor (not shown), and rotates plus or minus 185° in either direction from a home position 410.

Reagent transfer probes 402 and 404, which are identical to one another, preferably comprise automatic pipette metering/dispensing pick-up devices designed to aspirate or "sip" reagent from a reagent bottle, move to a slide, and then "spit" or deposit the reagent onto the slide. "Sip" and "spit" automatic pipette/metering dispensing pick-up devices are described in published PCT Application No. PCT/US99/04379, which disclosure is incorporated herein by reference. Reagent transfer probes 402 and 404 are carried on the distal end of arm 400 and are spaced from one another so that when one of the probes, e.g. probe 402 is located centrally over a slide 60, the other reagent transfer probe 404 may be centrally positioned over one of the two probe wash stations 121 or 122. A pneumatic cylinder (not shown) selectively raises and lowers probes 402 and 404 into one of the following positions: a raised transport position above the tops of the bottles 302 where the arm 400 is free to rotate; a reagent drawing position wherein one of the probes is inserted into a selected reagent bottle 302 wherein a measured amount of reagent may be drawn into the probe; a reagent dispensing position wherein a reagent transfer probe containing reagent is disposed in the pie-shaped space 326 between two reagent bottles, above a selected slide to dispense reagent thereon; and a cleaning position wherein the other probe, i.e. the probe not being used to dispense reagent, is operatively disposed in one of probe washing stations 121 or 122. While the apparatus of the present invention could be made with only a single reagent transfer probe, providing two spaced reagent transfer probes essentially doubles cycle speed since reagent metering may be accomplished using one of the two reagent transfer probes while the other of the two reagent transfer probes is going through the wash cycle as will be described below. That is to say, while one of the reagent transfer probes, e.g. reagent transfer probe 402 is dispensing reagent onto a slide, the other reagent transfer probe, i.e. idle reagent transfer probe 404 may be lowered to a probe wash station 121 where the idle reagent transfer probe may be rinsed inside and out at the same time.

Figure 10:
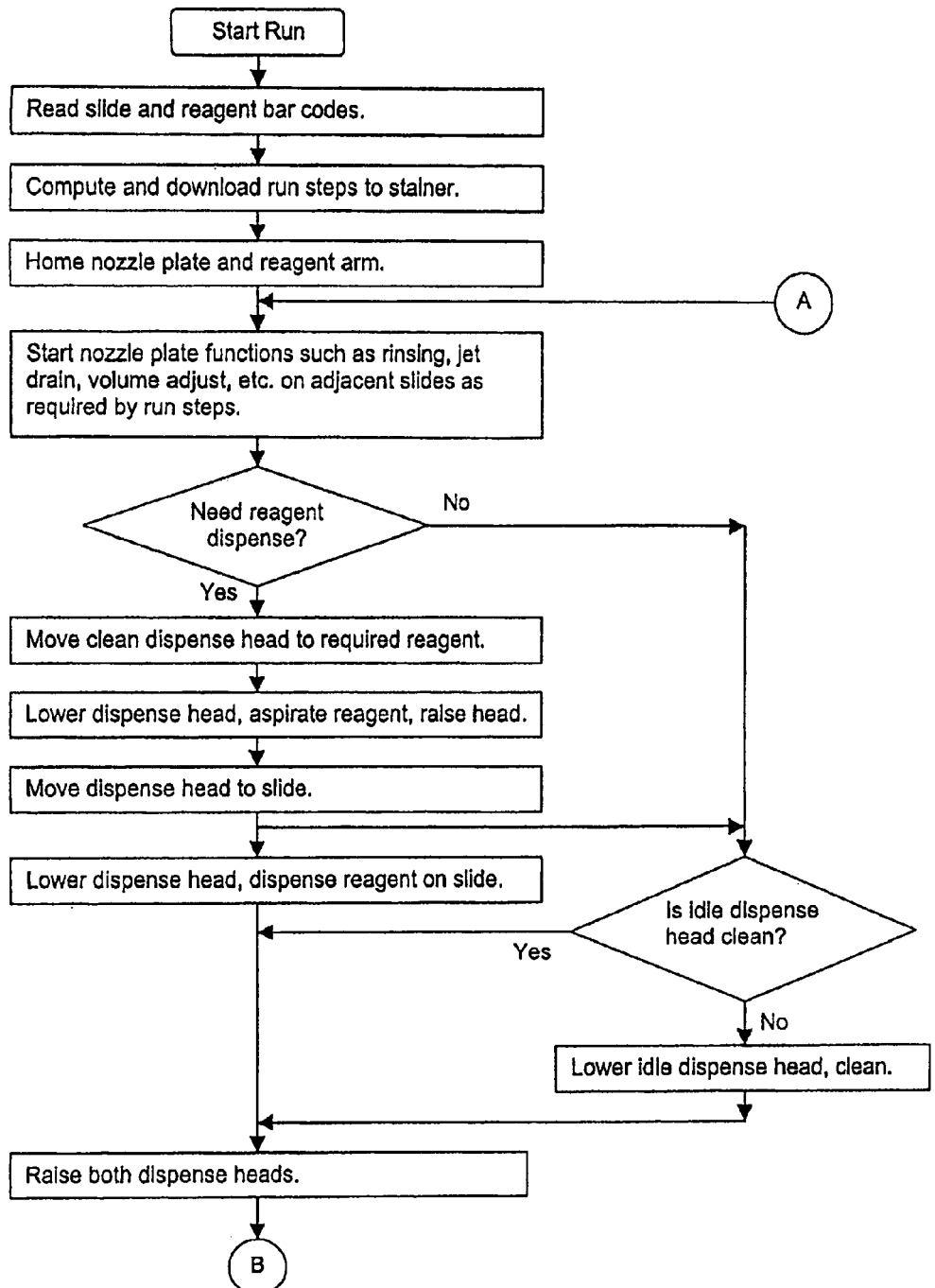
FIG. 10 is a flow chart of the operation and control of the present invention.
Figure 10:
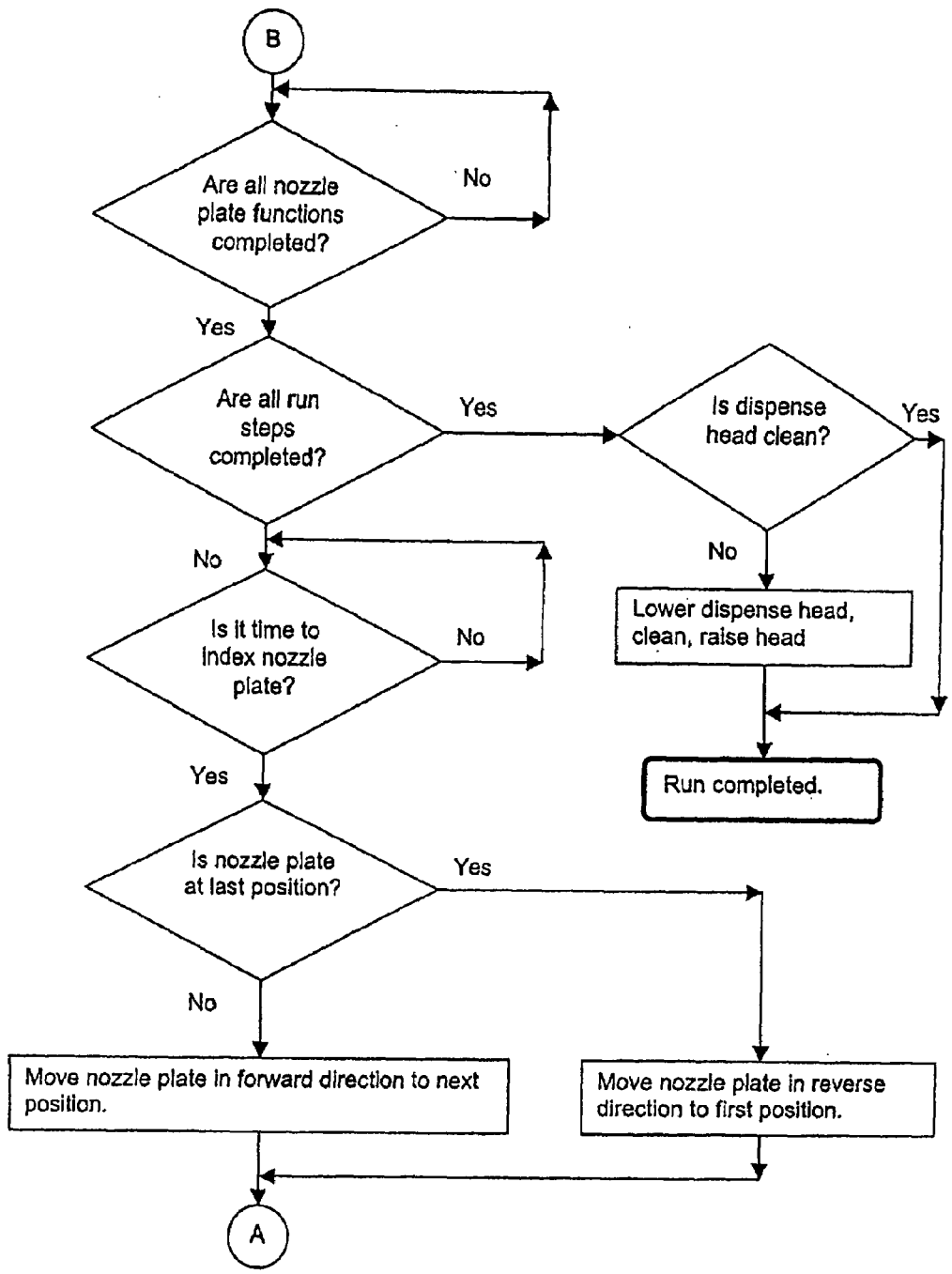

Referring to FIG. 10, the overall process is as follows:

A plurality of specimen-bearing slides 60 are mounted on the slide platforms 50, selected reagent bottles 302 mounted in the reagent plate, the slide drawer is closed and the slide bar codes are read. The computer than downloads the run steps for the entire run, the nozzle plate 100 is indexed to the first slide, and the slide is washed and prepared for staining or other treatment in accordance with the pre-programmed run steps by advancing the nozzle plate in "lock-step" manner. In the meanwhile, probe arm 400 is rotated to the appropriate reagent bottle 302, one of the two reagent transfer probes 402 or 404 is indexed over the selected reagent bottle, and the probe lowered to aspirate a measured amount of the desired reagent. The reagent-containing transfer probe is then raised, and the arm 400 moved to the selected slide where the loaded reagent transfer probe is lowered to just over the slide, and the reagent dispensed on the slide. In the meanwhile, the idle reagent transfer probe is lowered into one of the washing stations 121 or 122, wherein the reagent transfer probe is washed inside and out.

Both reagent transfer probes 402 and 404 are then raised, and the process repeated, but using the reagent transfer probe just cleaned in the previous step to aspirate and dispense reagent onto the next slide. As before, simultaneously with dispensing the reagent onto the slide as in the previous case, the idle reagent transfer probe is washed while the active reagent transfer probe is dispensing reagent onto the new slide.

The foregoing steps are repeated until all of the slides are processed. For convenience, in the illustrated embodiment, the dwell time at each slide station is approximately six and two-thirds seconds. This comes from dividing a four minute cycle time into thirty-six time spaces, one time space for each of the thirty slide positions plus five blank slide positions, plus one "virtual" time space for returning the arm 400 from the last slide position to the first slide position. The virtual slide position allows the nozzle plate to return to the other end of its travel range in an uninterrupted fashion.

The staining algorithm used on the aforesaid Ventana systems avoids the above problem by using a "lock step" method. The lock step algorithm requires that the nozzle plate which holds the processing functions be rotated one slide position index every n seconds, termed the slide index time. The slide index time is preferably as short as possible but long enough that the function that requires the longest time can be completed within the index time. Index times are usually on the order of several seconds. The time for one complete rotation of the nozzle plate, termed the fundamental incubation period, will then be n times the number of slide positions. (For example, if the slide index time is six seconds and there are twenty slide positions, the incubation time period will be 120 seconds or two minutes.)

Throughout the entire run the nozzle plate is indexed one slide position every n seconds. After the index, the system checks the schedule to see if any of the slides at each of the processing stations require the function of that station. For example, if the slide at the washing station is scheduled for washing, that slide is washed. Similarly if the slide at the reagent application station is scheduled for the application of a new reagent, then the new reagent is applied.

The above-described invention has several advantages over the prior art. For one, making the slide plate fixed in position reduces the possibility of a slide being dislocated during the rapid start-stop rotational movement of a slide carousel. Also, employing two transfer syringes insures better cleaning of transfer syringes without increasing cycle time. Also, using vials or bottles for reagents eliminates the prior art's reliance on complex and costly dispensers.

Also, since none of the moving elements, i.e. nozzle plate 100 and probe support arm 400 need travel more than plus or minus 185° in either direction, all electrical connections, and air and fluid connections can be achieved without the need for slip ring or rotary connections, since the hoses and wires are quite capable of taking twistings of 185° plus.

The instrumentation described herein may or may not have the ability to continuously rotate the nozzle plate. The nozzle plate may need to return to a starting position before rotation has exceeded 360 degrees. This may also be required when the slides are rotated on a carousel and the processing functions are fixed above the slides. Similarly, other non rotating designs are possible such as linear or two dimensional configurations. In these cases there will be a requirement to move the slides or processing functions back to the original starting position during the staining run. In most cases it is likely that the time required to do this will exceed the index time which violates the fundamental requirement of the lock step algorithm. The lock step algorithm can still be used by introducing the concept of a "virtual slide". The virtual slide is added to the total number of slides so that the index time period assigned to the virtual slide may be used to move the slides or processing stations back to the starting position. Thus accurate and predictable incubation times are maintained.

While a preferred embodiment of the invention has been described, the invention is susceptible to modification. For example, instead of using one or a pair of transfer syringes on an overhead arm, the reagent carousel could carry a plurality of micro-delivery reagent fluid dispensers such as described in U.S. Pat. No. 5,232,664 or 5,654,200 or 6,093,574 or 6,192,945. Moreover, while the use of individually heated thermal platforms is preferred, the slides may be heated using conventional convection heating techniques. Still other changes may be made without departing from the spirit and scope of the invention.

What is claimed is:

1. An automatic slide processing apparatus comprising:
   (a) a slide support tray slidably mounted on rails to permit loading and unloading of slides into and from the apparatus;
   (b) a reagent delivery tray;
   (c) a nozzle support plate concentrically mounted between said slide support tray and said reagent delivery tray; and
   (d) a reagent dispensing mechanism rotatably and concentrically mounted above said reagent delivery tray for selectively dispensing reagent on a slide carried on the slide support tray;
   wherein the slide support tray and the reagent delivery tray are operatively fixedly positioned in said apparatus, and the nozzle support plate is selectively rotatably operatively movable relative to the slide support tray and the reagent delivery tray, and wherein said slide support tray includes at least one liquid drain.

2. An apparatus as claimed in claim 1, wherein said slide support tray carries a plurality of radially spaced slide support platforms.

3. An apparatus according to claim 2, wherein said slide support platforms include heaters.

4. An apparatus according to claim 2, wherein said slide support platforms include temperature sensors.

5. An apparatus according to claim 1, and further including a damping mechanism for damping sliding movement on the rails.

6. An apparatus according to claim 1, wherein said rails are supported on a lift mechanism.

7. An apparatus according to claim 1, wherein said reagent dispensing mechanism is selectively moveable relative to the reagent delivery tray.

8. An apparatus according to claim 7, wherein said reagent dispensing mechanism comprises robotic dispensing pipettes.

9. An apparatus according to claim 8, wherein said dispensing pipettes are vertically moveable between an operating position and a transport position.

10. An apparatus according to claim 7, wherein said reagent dispensing mechanism is rotatably operatively movable over a range of 185° plus or minus from a home position.

11. An apparatus according to claim 1, wherein said nozzle support plate carries at least one vortex air jet.

12. An apparatus according to claim 1, wherein said nozzle support plate carries at least one air knife.

13. An apparatus according to claim 1, wherein said nozzle support plate carries at least one applicator for applying a cover fluid to the slide.

14. An apparatus according to claim 1, wherein said nozzle support plate is rotatably operatively movable over a range of 185° plus or minus from a home position.

15. An apparatus according to claim 1, and further comprising a reagent bar code reader carried with said reagent dispensing mechanism.

16. An apparatus according to claim 1, and further comprising a processor for controlling movement of said nozzle support plate and said reagent dispensing mechanism.

17. An apparatus according to claim 1, and further comprising a reagent dispensing mechanism wash station mounted on said nozzle support plate.

18. An apparatus according to claim 17, and comprising two reagent dispensing mechanism wash mechanisms mounted spaced from one another on said nozzle support plate.

19. An apparatus according to claim 1, wherein said slide support tray is operatively fixedly positioned relative to said reagent dispensing mechanism.

20. An automatic slide processing apparatus comprising:
 (a) a slide support tray slidably mounted on rails to permit loading and unloading of slides into and from the apparatus;
 (b) a reagent delivery tray;
 (c) a nozzle support plate concentrically mounted between said slide support tray and said reagent delivery tray; and
 (d) a reagent dispensing mechanism rotatably and concentrically mounted above said reagent delivery tray for selectively dispensing reagent on a slide carried on the slide support tray;
 wherein the slide support tray and the reagent delivery tray are operatively fixedly positioned in said apparatus, and the nozzle support plate is selectively rotatably operatively movable relative to the slide support tray and the reagent delivery tray, and wherein said reagent dispensing mechanism comprises two spaced robotic dispensing pipettes which are selectively movable relative to the reagent delivery tray.

21. An automatic slide processing apparatus comprising:
 (a) a slide support tray slidably mounted on rails to permit loading and unloading of slides into and from the apparatus;
 (b) a reagent delivery tray;
 (c) a nozzle support plate concentrically mounted between said slide support tray and said reagent delivery tray; and
 (d) a reagent dispensing mechanism rotatably and concentrically mounted above said reagent delivery tray for selectively dispensing reagent on a slide carried on the slide support tray;
 wherein the slide support tray and the reagent delivery tray are operatively fixedly positioned in said apparatus, and the nozzle support plate is selectively rotatably operatively movable relative to the slide support tray and the reagent delivery tray, and further comprising a slide bar code reader carried on said nozzle support plate.

22. An automatic slide processing apparatus comprising:
 (a) a slide support zone slidably mounted to permit loading and unloading of slides into and from the apparatus;
 (b) heating elements associated with the slide support zone for heating slides carried therein;
 (c) a reagent support zone; and
 (d) a nozzle support zone concentrically mounted between said slide support zone and said reagent support zone
 (e) a reagent dispensing mechanism operatively disposed to directly access both said slide support zone and reagent support zone, wherein said slide support zone and said reagent support zone are operatively fixedly positioned in said apparatus, and said reagent dispensing mechanism is selectively rotatably mounted above said reagent support zone and operatively movable relative to said slide support zone and said reagent support zone, and wherein said slide support zone includes at least one liquid drain.

23. An apparatus as claimed in claim 22, wherein said slide support zone carries a plurality of radially spaced slide support platforms.

24. An apparatus according to claim 23, wherein said slide support platforms include heaters.

25. An apparatus according to claim 23, wherein said slide support platforms include temperature sensors.

26. An apparatus according to claim 22, and further including a damping mechanism for damping sliding movement on the rails.

27. An apparatus according to claim 22, wherein said rails are supported on a lift mechanism.

28. An apparatus according to claim 22, wherein said reagent dispensing mechanism is selectively moveable relative to the reagent support zone.

29. An apparatus according to claim 28, wherein said reagent dispensing mechanism comprises robotic dispensing pipettes.

30. An apparatus according to claim 29, wherein said dispensing pipettes are vertically moveable between an operating position and a transport position.

31. An apparatus according to claim 28, wherein said reagent dispensing mechanism comprises two spaced robotic dispensing pipettes.

32. An apparatus according to claim 28, wherein said reagent dispensing mechanism is rotatably operatively movable over a range of 185° plus or minus from a home position.

33. An apparatus according to claim 22, and further including said nozzle support zone carrying at least one vortex air jet or at least one air knife above said slide support zone.

34. An apparatus according to claim 33, wherein said nozzle support zone carries at least one applicator for applying a cover fluid to the slide.

35. An apparatus according to claim 33, wherein said nozzle support zone is rotatably operatively movable over a range of 185° plus or minus from a home position.

36. An apparatus according to claim 22, and further comprising a slide bar code reader carried with said nozzle support zone.

37. An automatic slide processing apparatus comprising:
 (a) a slide support zone slidably mounted on rails to permit loading and unloading of slides into and from the apparatus;
 (b) heating elements associated with the slide support zone for heating slides carried therein;
 (c) a reagent support zone; and
 (d) a nozzle support zone concentrically mounted between said slide support zone and said reagent support zone
 (d) a reagent dispensing mechanism operatively disposed to directly access both said slide support zone and reagent support zone, wherein said slide support zone and said reagent support zone are operatively fixedly positioned in said apparatus, and said reagent dispensing mechanism is selectively rotatably mounted above said reagent support zone and operatively movable relative to said slide support zone and said reagent support zone and further comprising a reagent bar code reader carried with said reagent dispensing mechanism.

38. An apparatus according to claim 37, and further comprising said nozzle support zone and a processor for controlling movement of said nozzle support zone and said reagent dispensing mechanism.

39. An apparatus according to claim 37, and further comprising a nozzle support zone and a reagent dispensing mechanism wash station carried with said nozzle support zone.

40. An apparatus according to claim 39, and comprising a nozzle support zone and two reagent dispensing mechanism wash stations spaced from one another carried on said nozzle support zone.

41. An apparatus according to claim 37, wherein said slide support zone is operatively fixedly positioned relative to said reagent dispensing mechanism.

* * * * *